United States Patent [19]

Weinblatt

[11] Patent Number: 4,992,867
[45] Date of Patent: Feb. 12, 1991

[54] TECHNIQUE FOR MONITORING MAGAZINE READERS WHILE PERMITTING A GREATER CHOICE FOR THE READER OF POSSIBLE READING POSITIONS

[76] Inventor: Lee S. Weinblatt, 797 Winthrop Rd., Teaneck, N.J. 07666

[21] Appl. No.: 487,019

[22] Filed: Feb. 28, 1990

[51] Int. Cl.$^5$ ............................................. H04N 7/18
[52] U.S. Cl. .................................... 358/108; 358/93; 358/125
[58] Field of Search ............... 358/108, 139, 125, 226, 358/93

[56] References Cited

U.S. PATENT DOCUMENTS

| | | | |
|---|---|---|---|
| 3,158,431 | 11/1964 | Gutjahr et al. | 358/108 |
| 3,935,380 | 1/1976 | Coutta | 358/108 |
| 4,075,657 | 4/1978 | Weinblatt | 358/93 |
| 4,326,218 | 4/1982 | Coutta et al. | 358/108 |
| 4,661,847 | 4/1987 | Weinblatt | 358/108 |

FOREIGN PATENT DOCUMENTS 1241156 7/1971 United Kingdom ................ 358/108

Primary Examiner—John K. Peng
Assistant Examiner—Jeffrey S. Murrell
Attorney, Agent, or Firm—Frishauf, Holtz, Goodman & Woodward

[57] ABSTRACT

A technique for unobtrusively monitoring a person reading a magazine to determine what page of the magazine is being read. It is necessary to monitor both the magazine as well as the reader's eyes for this purpose. However, test results can be skewed if the reader is placed in an environment to which he is not accustomed. In order to permit the person a great deal of choice as to where to sit and in what sitting position so as to simulate a "natural" environment rather than a test environment, one or more cameras are positioned in the room. In addition at least one mirror is mounted on a wall. The camera may have a direct view of either the reader's eyes or the magazine. Whichever one of these is not directly visible to the camera can be picked up by way of a reflection from the mirror. Various adjustments to the camera are provided so that the reader can be kept in view regardless of where in the room he decides to sit and read.

20 Claims, 3 Drawing Sheets

TECHNIQUE FOR MONITORING MAGAZINE READERS WHILE PERMITTING A GREATER CHOICE FOR THE READER OF POSSIBLE READING POSITIONS

BACKGROUND OF THE INVENTION

This invention is directed to a technique for monitoring individuals reading a magazine and, more particularly, to determining which pages of an open magazine are examined by the reader and which are quickly skipped over.

It is important for publishers and advertisers to know which pages in a magazine are looked at attentively by a reader (used below interchangeably with "person" and "individual"). The word "magazine" is used herein to refer to any publication which when opened and placed flat on a surface presents a left page and a right page to the reader. It is well known that in the course of perusing a magazine, the attention of a reader will be attracted to certain pages and not at all to others. If an accurate and reliable method were available for determining whether the reader lingers on a given page, this information would be representative of the attraction to the reader of the contents of that particular page. Thus, for example, if an article appears on a given page, a measurement could be made by analyzing the extent to which a person's attention is drawn to that particular page. If such measurements indicate that the page does not draw the preferred degree of attention, then the caption of the article, for example, could be changed so that it becomes a stronger magnet for pulling the reader's attention to the article. Likewise, if an advertisement were to be placed on a given page, this test could be utilized to measure whether the advertisement is merely noticed and then quickly skipped over, or whether it succeeds in having the reader pay it the desired degree of attention. Such a technique is an important measurement tool for determining whether whatever is printed or displayed in the magazine functions to provide the level of exposure to the readership of the magazine that one expects by going to the expense of printing it.

The primary technique currently available to determine the level of attention devoted by a reader to a particular article or advertisement involves the interview method. A reader is selected as a test subject and asked to read a particular magazine. After the magazine is read, the person is then asked a number of questions about what was just read. However, this method is heavily dependent on recall, honesty and objectivity. It, therefore, may not accurately reflect what the reader actually experienced.

Another disadvantage of this type of technique currently in use is the unnatural, abnormal environment into which the person is placed while taking the test. The environment varies from that which the person is normally accustomed to while reading a magazine. As a result, the person may be nervous or distracted. Consequently, the test results may not be an accurate measurement of that person's reactions to the magazine under normal conditions.

Another technique for obtaining this information utilizes eye movement monitoring equipment. As described in the article "Methods & Designs, Survey of Eye Movement Recording Methods" by Laurence R. Young and David Sheena in Behavior Research Methods & Instrumentation 1975, Vol. 7(5), pages 397–427 and U.S. Pat. No. 4,075,657 issued Feb. 21, 1978, eye movement monitoring techniques bounce an infrared beam off the eye and detect the position of the reflected beam. Eye position is determined from the reflected beam position. Head position must be stabilized so that beam movement is due only to eye movement and not head movement. The eye position as indicated by the reflected beam is superimposed on an image of a magazine page. The page image can be obtained from a video camera aimed at the view displayed to the test subject.

Such equipment has several disadvantages. Firstly, equipment constraints are such that the head is pointing forward rather than downward in order to readily accommodate the infrared light source and the reflected beam detector. Therefore, a magazine would have to be placed vertically in front of a person. However, because this is not practical, slides are used to display the magazine pages. This requires extra slide equipment. Secondly, large size publications cannot be tested because of the limited angular range of eye rotation which eye movement monitoring equipment can measure (27"). Thirdly, persons wearing bifocals and contact lenses disperse the infrared beam. Fourthly, due to the unnatural head rigidity and head position required which is very different from that normally used for reading, a person may not read the text for as long a time as would be the case in the "real world". Fifth, eye movement monitoring equipment is relatively heavy and bulky and is, thus, not portable. Sixth, such equipment is visible to the person and can be obtrusive and distracting. Seventh, with the equipment being visible, the person must be told that a test is being performed which, consequently, may modify the reading habits and reactions to the magazine contents. All of these factors, singly or in combination, can detract from the accuracy of the test and are, therefore, preferably to be eliminated.

One other approach available for obtaining this information is disclosed in U.S. Pat. No. 4,661,847 issued Apr. 28, 1987 to the present inventor. It discloses a housing placed above a reading surface such as a desk top. The housing contains a lens aimable at the eyes of a test subject sitting at the desk, lenses aimed down at both sides of an open magazine, a mirror arrangement, and an optical image superimposition device for combining the eye and page images. This arrangement provides a significant improvement over the other techniques. However, because the housing is fixed in position above a reading surface on which the magazine is laid, the test subject is constrained in terms of having to sit at the desk. This reading position may be unnatural and uncomfortable to a particular test subject. Moreover, the level of discomfort can only increase the more time that must be spent in that position. Consequently, this approach does not adequately simulate conditions to which the individual would be subjected when reading a magazine under conditions considered normal. Because the testing conditions create an artificial situation, the test subject may produce commensurately inaccurate test results.

SUMMARY OF THE INVENTION

It is a primary object of the present invention to provide an improved technique for determining which pages of a magazine are read by a person selected as a test subject.

Another object of the present invention is to provide an accurate and reliable technique for determining which pages in a magazine are read by a person selected as a test subject.

A further object of the present invention is to provide a relatively simple, inexpensive yet effective technique for determining which pages in a magazine are read by a person selected as a test subject.

Yet another object of the present invention is to provide an accurate and reliable technique for determining which pages in a magazine are read by a person selected as a test subject without that person being aware that his reactions are being monitored.

Still another object of the present invention is to simulate a reading environment and conditions natural to the test subject so as to obtain more accurate test results.

These and other objects of the invention are attained by apparatus for monitoring an individual performing as a test subject who has been placed within a room and is reading a magazine. The apparatus includes camera means for recording an image. The camera is comprised of a lens and an image detecting means responsive to light from the lens for producing a signal representative of a recorded image. The camera means has (a) a first portion not visible to the test subject, and (b) a second portion at least partially visible to the test subject. A means is provided to direct light from an eye of the individual and from the magazine to the camera means. The light directing means includes first means positioned on a surface of the room for directing light it receives from one of the test subject and magazine toward the second portion of the camera means. An additional means is provided for adjusting the orientation of a field of view of the camera means to enable monitoring by the camera means of an eye of the individual and a magazine being read by the individual.

DETAILED DESCRIPTION OF THE PREFERRED EMBODIMENT

In order to provide the individual acting as the test subject with the maximum degree of ease and comfort in a "normal" setting, it is important to make available as much natural freedom of motion as possible as well as a variety of types of seating and sitting positions. It would be unnatural to confine the individual to a particular spot within a room and to a particular body position and reading position. Since tests conducted with the technique of the present invention typically involve a large number of individuals in order to obtain a statistically meaningful result, selecting a particular type of seat, in a certain part of the room and oriented in a given way might be comfortable for some individuals while, on the other hand, making other individuals ill at ease. It is impossible to satisfy a large number of individuals with a restricted set of room and seating conditions. As explained above, this is a deficiency of the technique disclosed in U.S. Pat. No. 4,661,847 which places the monitoring equipment above the surface of a desk thereby constraining the individual to sit at that desk and in a certain reading position. Thus, in order to make the individual as comfortable as possible and to thereby simulate as nearly as is possible the normal reading conditions for that individual, it is essential to provide a relatively large number of possible locations, orientations, sitting positions and types of seats. However, if the individual is given the maximum degree of freedom, the task still remains of being able to monitor the 15 magazine pages and the individual's eyes with equipment that must as of necessity be stationary and also not readily visible, or at least not detectable as being part of a monitoring apparatus.

Figure 1:
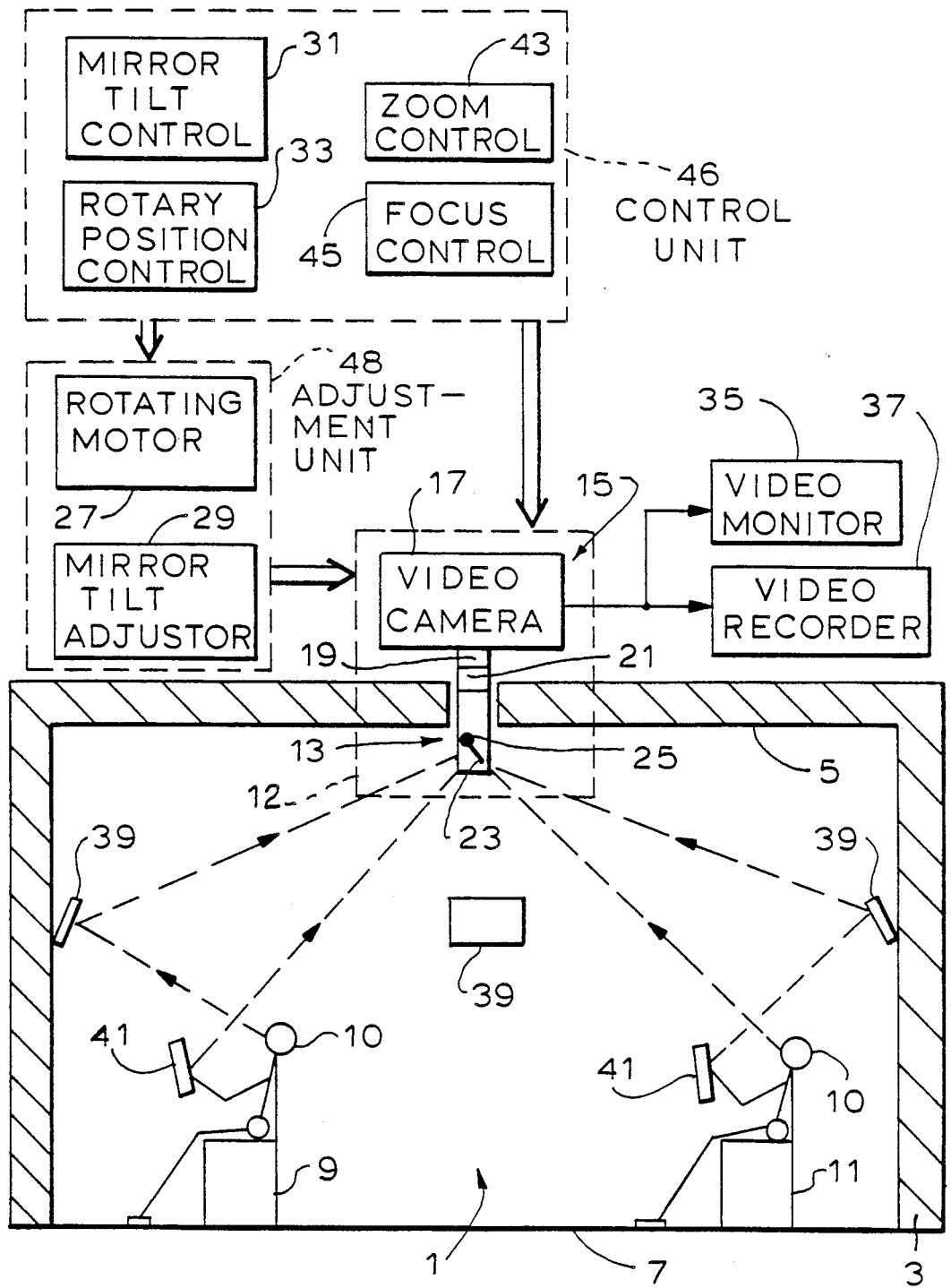
FIG. 1 shows a schematic circuit diagram and an elevational view of a room in which components of the invention are placed.

As shown in FIG. 1, the site for conducting the tests is a standard room 1 having walls 3, ceiling 5, and floor 7. Positioned around room 1 and resting on floor 7 is a selection of comfortable seating types. These are represented in FIG. 1 by two chairs 9 and 11 upon which individual 10 is seated. However, it will be recognized that these chairs are intended to represent the full array of seating type furniture that one could normally find in a home, such as a rocker, reclining chair, sofa, armchair, and so on. These are arranged relative to each other in the room in what could be termed a "typical" way which need not, of course, be discussed in detail herein. Suffice it to say that the room arrangement provides a variety of seating types, seating positions, and orientations.

The apparatus of the present invention includes a ceiling mounted camera means 12 one portion 13 of which protrudes below the ceiling while another portion of which, 15, extends through and above the ceiling. In conventional fashion, camera means 12 captures, or records, an image. It includes an image detecting means such as a CCD responsive to light for generating an electric signal corresponding to an optical image. Portion 13 of camera means 12 is configured to look like, for example, a smoke detector or, preferably, a sprinkler head. The object behind so configuring this device is as a disguise so that it is not readily apparent to the individual that monitoring equipment is in the room. Again, the object is to make the individual comfortable and to put him as much at ease as possible, but knowledge by the individual that such monitoring equipment is in operation may alter the desired effect.

Portion 15 of camera means 12 includes a video camera 17 equipped with zoom lens 19 and focus 21 of conventional design. These are respectively controllable by zoom control 43 and focus control 45. Portion 13 includes a mirror 23 that is tiltable up and down about a horizontal axis at its attachment point 25. The tilt of mirror 23 is adjustable with mirror tilt adjustment unit 29 to provide a field of view for camera means 12, the direction of which is at my selected acute angle with respect to vertical. Portion 13 is rotatable about its vertical axis by rotating motor 27. Mirror tilt adjustment unit 29 is controlled by mirror tilt control 31, while the rotating motor 27 is controlled by rotary position control 33. For the sake of convenience and brevity in the succeeding discussion herein, zoom control 43, focus control 45, mirror tilt control 31 and rotary position control 33 are grouped together as control unit 46, while mirror tilt adjustor 29 and rotating motor 27 are grouped together as adjustment unit 48.

The output signal from video camera 17 is provided to a video monitor 35 and also to a video recorder 37. An operator observes the image displayed on video monitor 35. The object sought to be obtained by the operator is to display on video monitor 35 both the image of at least one of the individual's eyes as the magazine is being read, as well as an image of the magazine itself. The image of the magazine shows the open magazine and, therefore, both sides (i.e. pages) of the magazine in the place to where it has been opened. The image of the individual's eyes reveals where on the open pages of the magazine the individual is looking. By superimposing the two images on each other it is possible to ascertain which of the two sides of the magazine is being looked at by the individual as well as what portion of that page is being read.

In order to assist the operator in acquiring the superimposed image mentioned just above, an important element is the provision of mirror 39 on at least one wall 3 of room 1. As shown by the depiction of the individual 10 seated on chair 9 and his particular reading orientation and position, the image of the magazine 41 is picked up directly by mirror 23 while the image of the individual's eyes is reflected by mirror 39 into mirror 23. If, on the other hand, the individual elected to sit in chair 11 in that particular seated position, then mirror 23 would directly pick up the image of the individual's eyes, while light from magazine 41 is reflected by mirror 39 into mirror 23. Consequently, the individual can sit anywhere in the room on any of the available seating types and in any reading position. The operator will rotate portion 13 and suitably tilt mirror 23 until the desired images are properly detected and superimposed. To assist in this respect, zoom control 43 and focus control 45 are also available to the operator for use in conventional fashion details of which are not deemed to be necessary. Mirror 39 is likewise necessary because it is unlikely that without it camera means 12 could obtain an image of the magazine as well as one of the person's eyes.

The number, size, vertical placement height, transverse wall position and downward tilt (if any) of mirror 39 cannot be specified as absolute values. These are heavily dependent on the parameters of the test room including its dimensions and the manner in which the furniture is arranged. If only one seat is provided, perhaps only one mirror 39 would suffice. More mirrors are commensurately required with the inclusion of additional furniture. Only an empirical determination can thus be made in this regard, and doing so is deemed readily apparent to one with ordinary skill in the art. Too many mirrors in the room should be avoided because that may arouse some suspicion in the individual.

Camera means 12 is preferably a unit available from Video Methods, Inc. ("VMI" hereinafter) of Westwood, NJ as its Model CTPZ1275CCD. This VMI equipment includes the camera means and related adjustment and control elements, other than for tilting mirror 23. A motorized mechanism for accomplishing such mirror tilting is readily apparent to one with ordinary skill in the art, and thus providing details thereof is not deemed necessary.

In operation, the individual who will be acting as the test subject is invited into the room on some pretext. Magazines, or just a magazine, are made available in the room. Nothing is said or done to the individual to indicate that a test is under way. Alternatively, one type of test might involve providing a selection of magazines, and the individual is asked to read one or more of the magazines of his choice in preparation for some questions he will be asked to answer later. However, the individual is not told that his actions in reading the magazines will be monitored. Whichever testing approach is used, it is important that nothing in the room gives away the fact that it has been customized and outfitted with special monitoring equipment. Thus, the individual sooner or later will sit down somewhere (anywhere), pick up a magazine and will start reading. The operator can monitor the individual's behavior by panning back on the zoom to get a wide field and suitably rotating portion 13. Once the individual sits down and begins to read, the zoom and focus are adjusted together with the rotary position of portion 13 and the tilt of mirror 23 until the desired superimposition of the reader's eyes on the magazine is obtained. Should the reader shift position on chair 9, for example, or perhaps even switch to chair 11, the operator will simply follow him with the equipment described above to reacquire the desired images of magazine and eyes.

Figure 2:
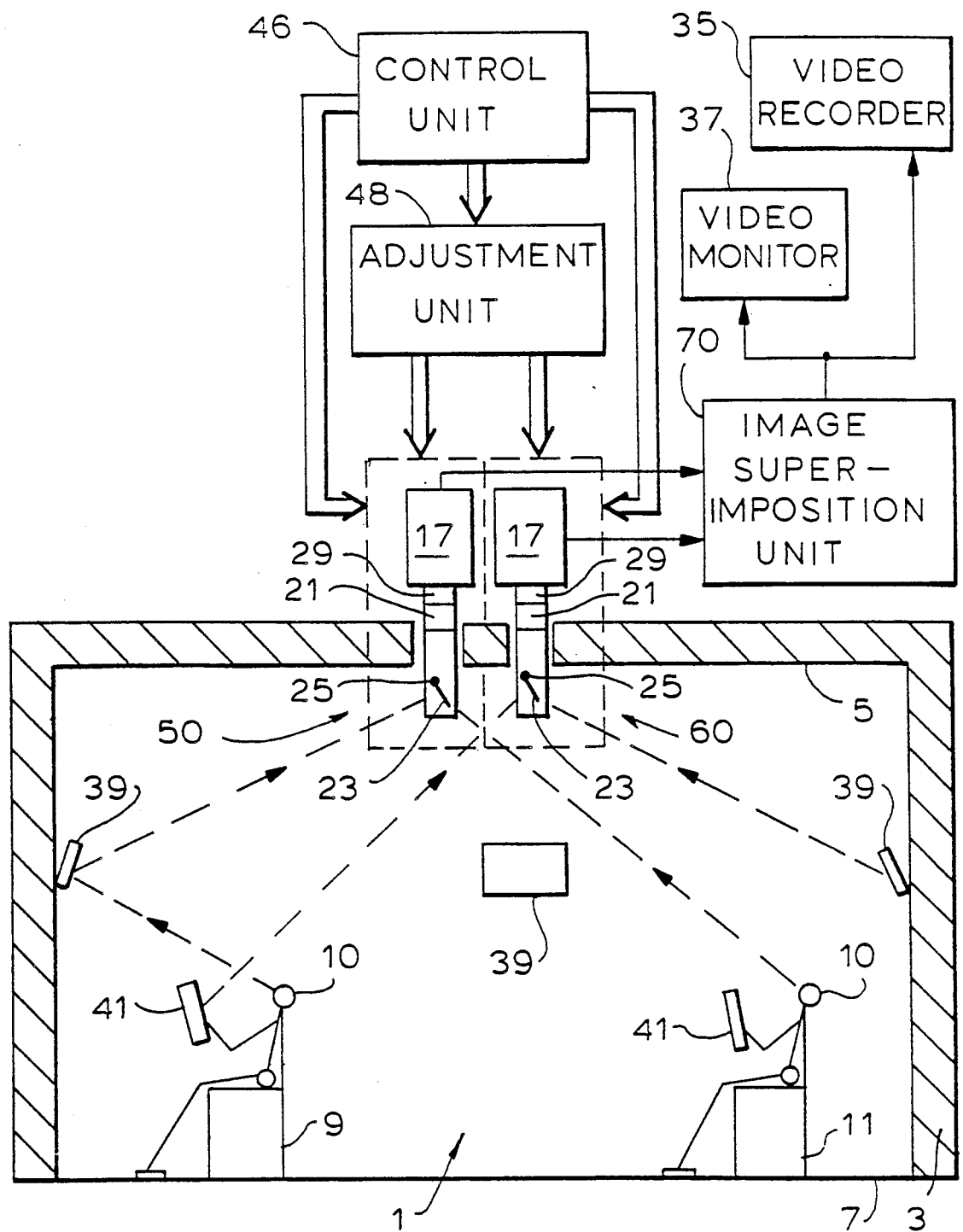
FIG. 2 is similar to FIG. 1, and shows a second embodiment of the invention.

A second embodiment of the present invention is depicted in FIG. 2. Components common to FIGS. 1 and 2 have been assigned the same numbers. Whereas the FIG. 1 embodiment shows a single camera means for viewing both the magazine and the individual's eyes, the FIG. 2 embodiment splits these tasks between two camera means 50 and 60. Each of these camera means and the associated adjustment and control means is identical to that which is shown in FIG. 1 and described in detail above. Consequently, it is not deemed necessary to repeat that description here. Thus, as is readily evident from FIG. 2, for the position of the reader 10 seated in chair 9, camera means 60 monitors the magazine while camera means 50 monitors the individual's eyes by way of light reflected by mirror 39. On the other hand, should the individual have elected to sit in chair 11, then camera means 60 would monitor the magazine by way of light reflected into it from mirror 39, whereas camera means 50 would have a direct view of the individual's eyes. Which of camera means 50, 60 monitors one or the other of the magazine and the eyes depends on the operator's judgment as to how the best image of each is obtained. Of course, certain situations may arise where only one of the camera means can get a good view. For example, if the reader seated in chair 11 were to drop the magazine to his knees, his head may block camera means 60 from a view of the magazine via mirror 39. In that case, camera means 60 would be used to view the magazine while camera means 50 would obtain a direct view of the reader's eyes.

The output signal from the respective video cameras of camera means 50 and 60 are input to an image superimposition unit 70. This is a conventional device known generically as a signal effects generator and it is available from major electronics manufacturers such as Sony and JVC. The output from unit 70 is then provided to a video monitor and a video recorder as is the case with the FIG. 1 embodiment. The FIG. 2 embodiment provides greater flexibility and versatility because certain constraints (dependent on the specific room and furniture dimensions and arrangement) are imposed by the FIG. 1 system in terms of the distance and angle of the reader's eyes and the magazine relative to mirror 39 in order to be able to get images of both the magazine and the eyes with the same camera means. However, with the use of two individual cameras as is the case with the FIG. 2 embodiment, such constraints are minimized if not totally eliminated.

Figure 3:
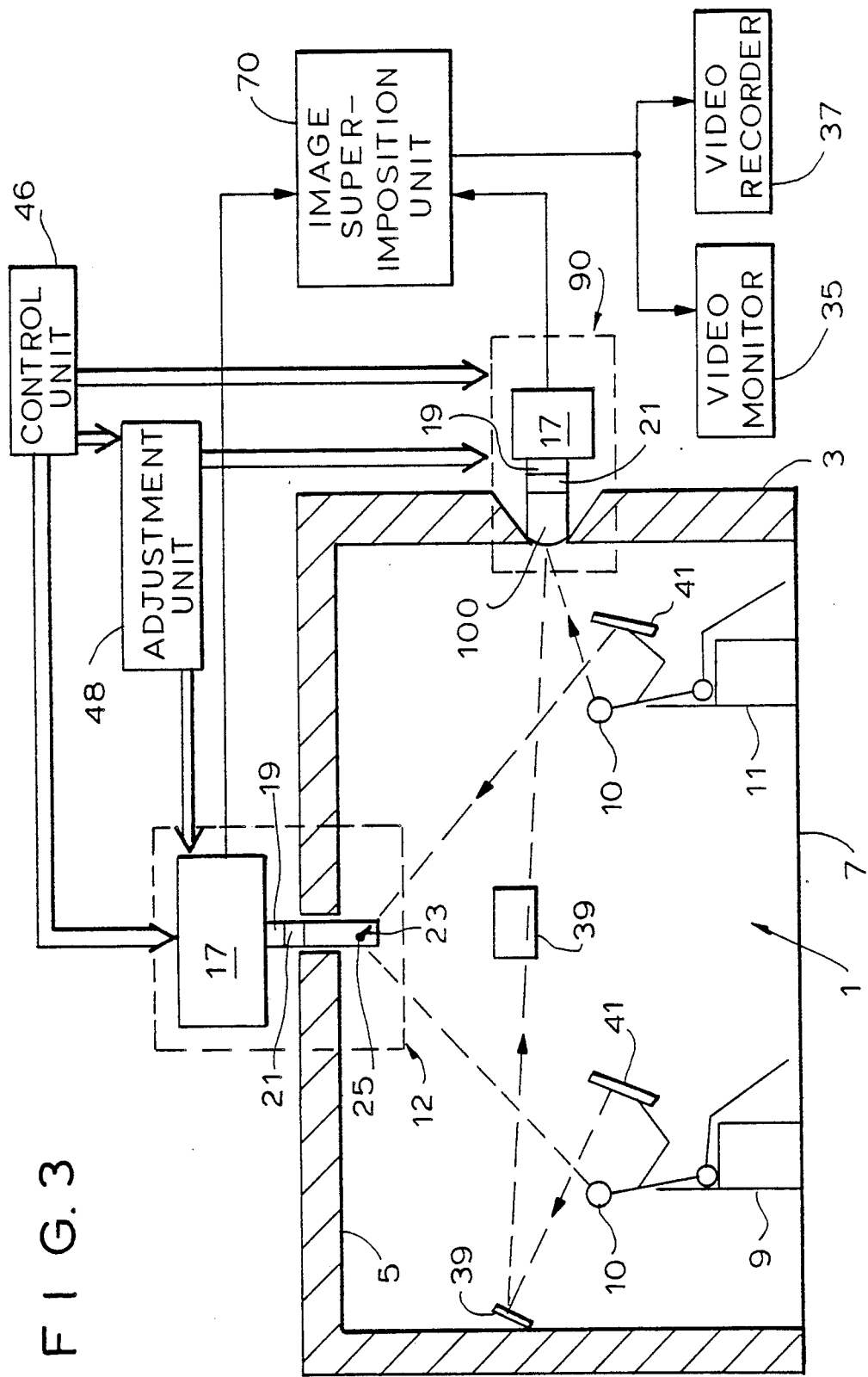
FIG. 3 is similar to FIG. 1, and shows a third embodiment of the invention.

A third embodiment of the present invention is depicted in FIG. 3. It shows a camera means 12 (same one as shown in FIG. 1) mounted in the ceiling, as in the previously discussed embodiment, and a camera means 90 mounted in a wall of room 1. Camera means 90 cannot, for obvious reasons, be camouflaged on a wall with a sprinkler head in the manner used for the ceiling mounted versions. Consequently, camera means 90 must have a front element 100 that presents minimum exposure to anyone in the room. The front element 100 is thus "obscured" by virtue of its small size. The SL0800 series of lenses available from the above-mentioned VMI requires a hole through the wall as small as ¼ inch. This lens is provided with controllable zoom and focus. Also, the lens assembly can be tilted vertically and horizontally using the front face as its fulcrum of motion so that an adequate panning range is provided. The tilting apparatus involves the use of gearing and tracks combined with motors. Various specific arrangements can be added all of which are readily apparent to one with ordinary skill in the art.

The combination of camera means 12, camera means 90 and mirrors 39 provides one more way of monitoring both the magazine pages and the individual's eyes so that the two can be superimposed to provide the information being sought. The two images are superimposed in image superimposition unit 70 which functions in the same manner as the corresponding unit 70 in the FIG. 2 embodiment. When reader 10 is seated in chair 11 magazine is not visible to camera means 90. Thus, it will monitor the reader's eyes while camera means 12 monitors the magazine. On the other hand, when reader 10 sits in chair 9, his eyes are blocked from camera means 90 by the position in which magazine 41 is being held. Thus, camera means 12 will monitor the reader's eyes while the magazine is visible to camera means 90 via mirror 39.

Although preferred embodiments of the present invention have been described in detail above, various modifications thereto will be readily apparent to one with ordinary skill in the art. For example, in the FIG. 3 embodiment, it may be advantageous to provide a mirror on ceiling 5 rather than to restrict the positioning of mirrors 39 only to walls 3. The disadvantage of putting a mirror on the ceiling is that it may appear suspicious to the individual unless it is suitably camouflaged. It may also be possible to selectively control the tilt of wall mounted mirrors 39 by the operator to provide one additional adjustment variable in order to facilitate obtaining superimposed image of both the magazine and the individual's eyes. Furthermore, although the discussion presented above constantly talks about the individual being seated, it goes without saying that should the individual choose to stand while reading the magazine, the monitoring operation can also be carried out. In addition, the pinhole camera of the FIG. 3 embodiment is also usable for implementing the FIGS. 1 and 2 embodiments. Likewise, the ceiling mounted camera of FIG. 1 can be used for the wall mounted camera of FIG. 3 if the visibly protruding portion is somehow hidden, obscured or camouflaged. Specific camera means from VMI have been mentioned. However, any camera means can be used as long as it combines the requisite adjustments that are necessary to obtain an image of both the magazine and the reader's eyes, but the visible portion must be camouflaged or obscured. It is also readily apparent that one or more of the variety of adjustment features mentioned above could be eliminated if found to be superfluous to the particularitis of the test site. Thus, for example, the operator-controlled tilting of mirror 23 could possibly be dispensed with. Also, perhaps the vertical tilt of camera means 90 in the FIG. 3 embodiment is unnecessary. These and other such modifications ar all intended to be included within the scope of the present invention as defined by the following claims.

I claim:

1. Apparatus for monitoring an individual performing as a test subject who has been placed within a room and is reading a magazine, comprising:
   camera means for recording an image and including a lens and an image detecting means responsive to light from said lens for producing a signal representative of a recorded image, said camera means having (a) a first portion not visible to the test subject, and (b) a second portion at least partially visible to the test subject;
   means to direct light from an eye of said individual and from said magazine to said camera means, said light directing means including first means positioned on a surface of said room for directing light it receives from one of said test subject and said magazine toward said second portion of the camera means; and
   means for adjusting the orientation of a field of view of said camera means, after said individual is seated at any one position selected by the individual out of a plurality of seating positions in said room, to enable monitoring by said camera means of the at least an eye of the individual and said magazine being read by the individual.

2. The monitoring apparatus of claim 1, wherein aid camera means is mounted in the ceiling of said room.

3. The monitoring apparatus of claim 1, wherein said camera means is a single camera.

4. The monitoring apparatus of claim 1, wherein said camera means is comprised of two cameras, one being aimed at the at least one eye of the individual test subject and the other being aimed at the magazine.

5. The monitoring apparatus of claim 4, wherein both of said cameras are mounted in the ceiling of said room.

6. The monitoring apparatus of claim 4, wherein one of said two cameras is mounted in the ceiling and the other one is mounted in a wall of said room.

7. The monitoring apparatus of claim 1, wherein said light directing means further includes second means for directing light from at least one of the individual and the magazine to said image detecting means.

8. The monitoring apparatus of claim 7, wherein said second means of the light directing means sets the direction of the field of view of the camera means to be at an acute angle to vertical, and said orientation adjusting means rotates said direction of the field of view around a vertical axis to enable viewing of different portions of the room.

9. The monitoring apparatus of claim 8, wherein said second means of the light directing means includes a first mirror means vertically tiltable about a horizontal axis for varying the angle between vertical and the direction of the field of view, and said orientation adjusting means includes means for adjusting such vertical tilt.

10. The monitoring apparatus of claim 9, wherein said first mirror means is mounted in said second portion of the camera means.

11. The monitoring apparatus of claim 10, wherein said orientation adjusting means aims the second means to simultaneously receive light from the at least one eye of the individual and from the magazine.

12. The monitoring apparatus of claim 11, further comprising a zoom control means.

13. The monitoring apparatus of claim 12, further comprising a focus control means.

14. The monitoring apparatus of claim 13, further comprising a tilt control means coupled to the orientation adjusting means.

15. The monitoring apparatus of claim 14, further comprising a rotary position control means coupled to the orientation adjusting means.

16. The monitoring apparatus of claim 15, wherein said camera means is a single camera.

17. The monitoring apparatus of claim 15, wherein said camera means is comprised of two cameras, one being aimed at the at least one eye of the individual test subject and the other being aimed at the magazine.

18. The monitoring apparatus of claim 17, wherein each of said two cameras is independently controllable by the zoom control means, focus control means, tilt control means, and rotary position control means.

19. The monitoring apparatus of claim 18, wherein both of said cameras are mounted in the ceiling of said room.

20. The monitoring apparatus of claim 18, wherein one of said two cameras is mounted in the ceiling and the other one is mounted in a wall of said room.

* * * * *